(12) United States Patent
Yano et al.

(10) Patent No.: US 9,483,048 B2
(45) Date of Patent: Nov. 1, 2016

(54) SAMPLE TRANSPORT SYSTEM AND METHOD FOR CONTROLLING THE SAME

(75) Inventors: Shigeru Yano, Hitachinaka (JP); Koji Kamoshida, Hitachinaka (JP); Hiroshi Ohga, Hitachiomiya (JP); Tadao Shimizu, Ibaraki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 476 days.

(21) Appl. No.: 13/980,897

(22) PCT Filed: Jan. 18, 2012

(86) PCT No.: PCT/JP2012/051001
§ 371 (c)(1),
(2), (4) Date: Aug. 6, 2013

(87) PCT Pub. No.: WO2012/102156
PCT Pub. Date: Aug. 2, 2012

(65) Prior Publication Data
US 2013/0310964 A1   Nov. 21, 2013

(30) Foreign Application Priority Data

Jan. 26, 2011  (JP) .................................. 2011-013567

(51) Int. Cl.
*G05B 19/418*   (2006.01)
*G01N 35/00*   (2006.01)
(Continued)

(52) U.S. Cl.
CPC ....... *G05B 19/4189* (2013.01); *G01N 35/0092* (2013.01); *G01N 35/026* (2013.01); *G01N 35/04* (2013.01)

(58) Field of Classification Search
CPC ......... G05B 19/4189; G01N 35/0092; G01N 35/04; G01N 35/026

USPC .......... 700/112, 219–224, 228, 230; 422/63, 422/65
See application file for complete search history.

(56) References Cited

U.S. PATENT DOCUMENTS 5,269,646 A * 12/1993 Focke ..................... B65H 19/12
414/788.4
5,350,564 A * 9/1994 Mazza ................ B01L 3/50855
422/562
(Continued)

FOREIGN PATENT DOCUMENTS

JP          04172253 A *   6/1992     ............. G01N 35/02
JP          08-220105 A    8/1996
(Continued)

OTHER PUBLICATIONS

International Preliminary Report on Patentability received in International Application No. PCT/JP2012/051001 dated Aug. 8, 2013.

*Primary Examiner* — M. N. Von Buhr
(74) *Attorney, Agent, or Firm* — Mattingly & Malur, PC

(57) ABSTRACT

The sample transport system includes a management section which holds information on the status of a sample transport system as a whole as well as sample information in order to transport and control a plurality of carriers as a consecutive group and which generates group information on a group of carriers to be handled simultaneously based on sample attributes and request information; and units made up of a conveyer line, a connecting line, and a processing section to control received carriers at a converging point based on the group information, so as to permit group management control of the carriers. In this manner, the sample transport system processes as a single batch a plurality of samples collected for the same processing purpose.

10 Claims, 6 Drawing Sheets

(51) Int. Cl.
*G01N 35/02* (2006.01)
*G01N 35/04* (2006.01)

(56) References Cited

U.S. PATENT DOCUMENTS

| | | | | | |
|---|---|---|---|---|---|
| 5,351,801 | A | * | 10/1994 | Markin | B65G 37/02 198/346.1 |
| 5,445,037 | A | * | 8/1995 | Itoh | G01N 35/021 73/864.25 |
| 5,614,415 | A | * | 3/1997 | Markin | G01N 35/0092 422/65 |
| 5,730,276 | A | | 3/1998 | Itoh | |
| 5,794,213 | A | * | 8/1998 | Markman | D06F 95/00 705/22 |
| 5,966,309 | A | * | 10/1999 | O'Bryan | G01N 35/021 198/617 |
| 6,117,683 | A | * | 9/2000 | Kodama | G01N 35/00584 422/65 |
| 6,141,602 | A | * | 10/2000 | Igarashi | G01N 35/0092 422/561 |
| 6,261,521 | B1 | * | 7/2001 | Mimura | G01N 35/04 422/63 |
| 7,566,665 | B2 | * | 7/2009 | Inoue | C23C 14/56 438/16 |
| 8,428,770 | B2 | * | 4/2013 | Lund | G05B 19/41895 104/88.01 |
| 8,915,421 | B2 | * | 12/2014 | Lavi | G06K 19/07716 235/375 |
| 2002/0108857 | A1 | * | 8/2002 | Paschetto | B01L 3/0244 204/457 |
| 2003/0111494 | A1 | * | 6/2003 | Lin | B01L 3/0217 222/505 |
| 2007/0254277 | A1 | * | 11/2007 | Scrabeck | G06F 19/366 435/4 |
| 2008/0069730 | A1 | * | 3/2008 | Itoh | G01N 35/026 422/65 |
| 2008/0113440 | A1 | * | 5/2008 | Gurney | G01N 1/312 436/48 |
| 2010/0004779 | A1 | * | 1/2010 | Markin | G01N 35/00584 700/227 |
| 2012/0177548 | A1 | * | 7/2012 | Suzuki | G01N 35/026 422/548 |
| 2013/0027185 | A1 | * | 1/2013 | Lavi | B01L 9/06 340/10.1 |
| 2014/0294699 | A1 | * | 10/2014 | Akutsu | G01N 35/04 422/551 |
| 2015/0132798 | A1 | * | 5/2015 | Fox | G01N 35/0095 435/40.5 |

FOREIGN PATENT DOCUMENTS

| | | |
|---|---|---|
| JP | 09-043246 A | 2/1997 |
| JP | 09-043249 A | 2/1997 |
| JP | 11-281652 A | 10/1999 |
| JP | 2000-146988 A | 5/2000 |
| JP | 3579517 B2 | 7/2004 |
| JP | 2007-040932 A | 2/2007 |
| JP | 4486006 B2 | 4/2010 |

* cited by examiner

Fig. 2

|  | SAMPLE 1 | SAMPLE 2 | SAMPLE 3 | SAMPLE 4 | SAMPLE 5 | SAMPLE 6 | SAMPLE 7 |
|---|---|---|---|---|---|---|---|
| 201 — ID | S02001 | S02002 | S02003 | S02004 | S02005 | S02006 | S02007 |
| 202 — GROUP | 1 | 2 | 2 | 3 | - | 1 | 3 |
| 203 — UNIT | A, B | A, B | A, C, D | A, B | E | A, D | D |
| 204 — IMPORT PRIORITY | 1 | 1 | 1 | 1 | 1 | 10 | 10 |
| 205 — EXPORT PRIORITY | 1 | 1 | 1 | 1 | 1 | 2 | 2 |

SAMPLE TRANSPORT SYSTEM AND METHOD FOR CONTROLLING THE SAME

TECHNICAL FIELD

The present invention relates primarily to a sample transport system. More particularly, the invention relates to a sample transport system that uses carriers each capable of carrying a single test tube containing a testing sample such as blood or urine, as well as to a control method for causing the system to transport a plurality of testing samples collected from one patient as a consecutive group so that a plurality of test tubes may be simultaneously processed by the sample transport system that offers enhanced processing capability.

BACKGROUND ART

With the widespread use of laboratory test ordering systems, the number of test items requested by the doctor in charge of a patient may lead to automatic calculation of the amount of samples to be collected, whereby the number of test tubes for collecting samples from the patient is determined. A plurality of these test tubes containing the collected samples may contain the same type of sample for the same process. These samples are generally called multiple test tube samples, with the same sample barcode ID pasted on the test tubes containing the samples. One of the purposes of collecting multiple test tube samples is to alleviate the burdens on the patient who might otherwise be subjected to repeated sample collection in case of a sample being found to be insufficient in quantity after tests have started.

The sample transport system uses carriers each capable of carrying one or a plurality of test tubes containing testing samples such as blood or urine in particular, and transports the test tubes to a target processing unit. Conventional sample transport systems that use carriers each capable of carrying a plurality of test tubes could implement the same processing on the samples as each other by loading the system in question with one carrier transporting multiple test tube samples.

The sample transport system provided by Patent Literature 1 establishes purpose-specific carriers each capable of carrying a plurality of test tubes, thereby implementing simultaneous processing in handling multiple test tube samples and in aliquoting them in particular.

There exists another sample transport system, such as one provided by Patent Literature 2, which uses racks each capable of holding a plurality of test tubes and which has a plurality of carriers mounted on a loading section, the carriers being defined as a rack group. The system is designed to extract one rack after another, which can be processed by referring to system load information.

Meanwhile, the sample transport systems that use carriers each transporting only one test tube have not implemented performing the same processing as each other on the samples contained in a plurality of sample test tubes. One reason for this is that despite the presence of a blood collecting system or a testing system which manages the number of samples collected from each patients so as to identify the test tubes to be identically processed, a control system has yet to be established, which would allow these test tubes to be transported and handled for the purpose of identical processing.

As a background of the above circumstances, the sample transport systems utilizing carriers each carrying only one test tube could shorten processing time and deal with various modes of operation by letting the transport destination of each carrier be selected flexibly in accordance with system status. However, there was a possibility that the conveyor line in use could be occupied by multiple carriers being transported.

PRIOR ART LITERATURE

Patent Literature

Patent Literature 1: Japanese Patent No. 4486006
Patent Literature 2: Japanese Patent No. 3579517

SUMMARY OF THE INVENTION

Problems to be Solved by the Invention

The sample transport system of Patent Literature 2 does not implement transportation or control of the rack group inside the system.

A dedicated carrier may be used to process multiple test tube samples, whereby a plurality of samples collected from one patient for the same test purpose may be processed. Principally, this process is implemented using a rack capable of holding, say, five or 10 test tubes as a carrier for transporting the multiple samples.

However, this process utilizes the above-mentioned dedicated rack, so that the operator needs to handle the multiple test tube samples in steps different from those for ordinary samples. Furthermore, the rack capable of holding a plurality of samples may leave some of its positions vacant, which can lead to reduced efficiency in processing the ordinary samples.

In the case of a single carrier system with each carrier capable of holding only one test tube, there occurs no reduced processing efficiency stemming from the positions left vacant on the rack. However, with each carrier transported independently, there has yet to be established any mechanism or method for transporting a plurality of carriers as a consecutive group. Furthermore, there is a possibility that flexibility in single carrier transportation may be reduced.

In view of the above problems, one object of the present invention is to provide a sample transport system which, with no special steps to be taken, transports a plurality of mutually related samples consecutively so as not to let the processing efficiency of a processing section drop.

Means for Solving the Problem

The present invention is principally characterized to include: a management section which holds information on the status of a sample transport system as a whole as well as sample information in order to transport and control a plurality of carriers as a consecutive group, and which generates group information on a group of carriers to be handled simultaneously based on sample attributes and request information; and units which are made up of a conveyer line, a connecting line, and a processing section, and which control received carriers at a converging point based on the group information, thereby permitting group management control of the carriers.

Also, through the use of a wait buffer at the converging point, each group may be divided, or the divided groups may be merged again.

Effects of the Invention

The present invention provides a sample transport system which uses carriers each transporting one test tube and which forms a group of carriers into a single batch, the system being characterized in that another carrier may be controlled not to cut into a given group and the group division may be controlled, with group management performed in such a manner as to let a unit processing section carry out simultaneous processing of samples, thereby contributing to an increase in processing efficiency and reductions of manual processing. Furthermore, by selectively limiting the effective area of a given group, it is possible to minimize the range of group control and thereby minimize the influence of such group control on other ordinary samples, whereby the decline in processing efficiency is prevented.

BRIEF DESCRIPTION OF THE DRAWINGS

FIG. 2 shows group management control information.

MODE FOR CARRYING OUT THE INVENTION

Figure 1:
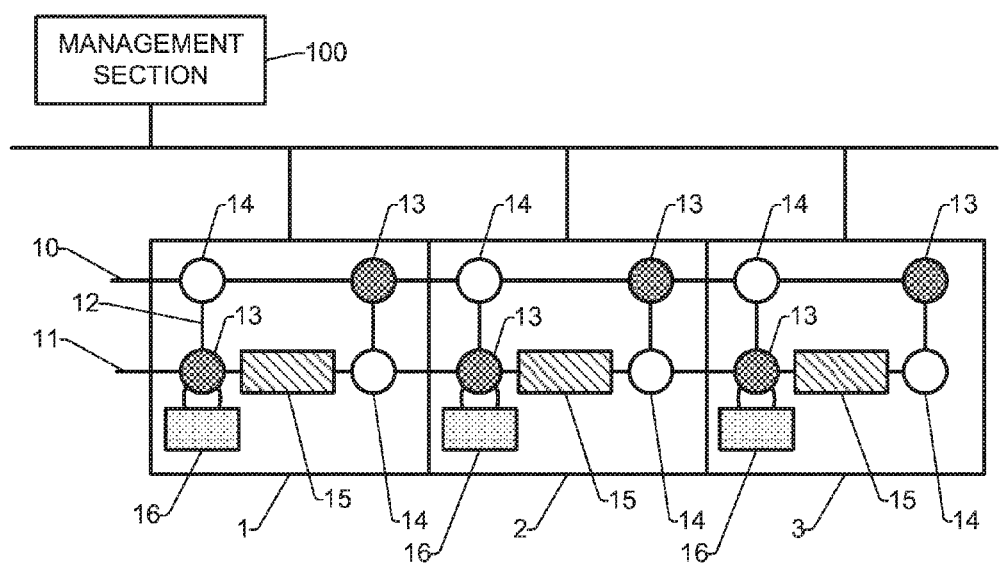
FIG. 1 shows a conveyor line model of a sample transport system.
Figure 5:
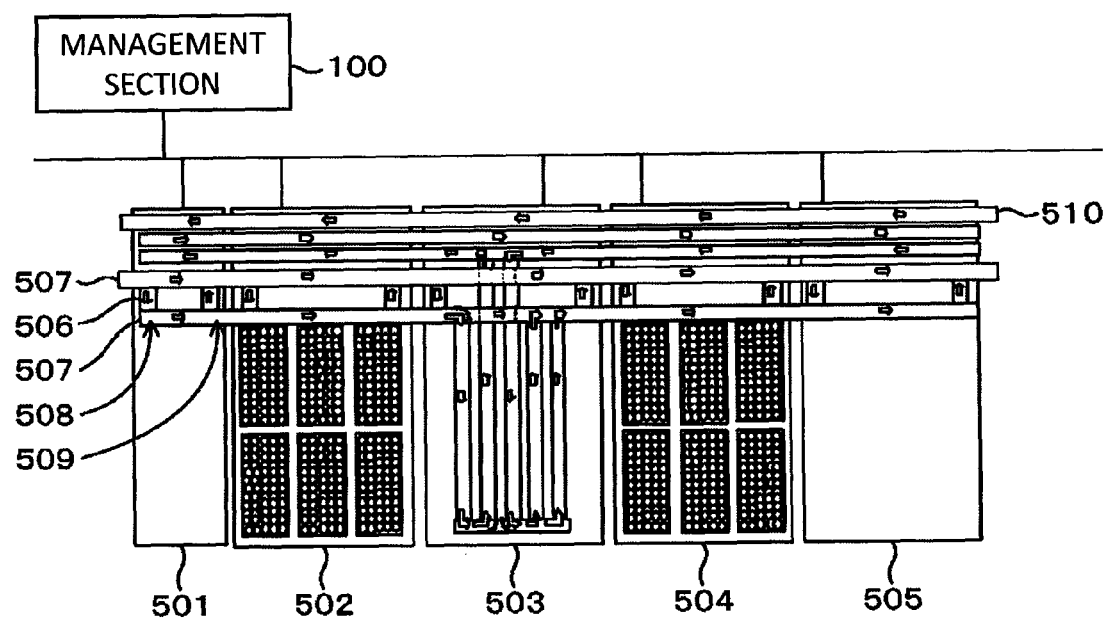
FIG. 5 is a general view of a sample transport system.

FIG. 1 shows a transport model of a sample transport system. FIG. 5 is a system general view of a specific sample transport system.

In the sample transport system of this embodiment, a plurality of pre-treatment units 1, 2, 3 is connected to each other. A sample placed on a carrier is transported by a conveyor line 11 and a connecting line 12 to each pre-treatment unit for necessary processing. Combining the conveyor line 11 with the connecting line 12 forms a converging point 13 and a branching point 14.

Incidentally, there exist a main conveyor line 11 that transports samples downstream from left to right as viewed in FIG. 1 and a return line 10 that transports the samples, which have been processed, downstream from right to left. On each of the lines 10 and 11, the converging point 13 is located upstream of the branching point 14.

Upon receipt of a sample to be managed as part of a group, the converging point 13 fixes the line from which the subsequent samples are received until their group management comes to an end. This makes it possible selectively to fix the source from which the samples are transported to the converging point 13. The received sample and the other samples belonging to the same group as that of the received sample can thus be imported consecutively into a unit processing section 15.

When the samples having been processed by the processing section are exported from the pre-treatment unit of interest, group management information is again set for the samples at the branching point 14. The steps involved here will be discussed later in detail.

When a sample loading section loads samples, a management section 100 determines whether or not the loaded samples need group management control based on sample attributes and sample request information, and creates initial group management control information. Each samples loaded by the sample loading section are notified of the group management control information together with destination information indicating the pre-treatment unit constituting the destination to which the sample in question is to be transported.

The group management control information is created when, for example, a plurality of samples collected from one patient for the same test purpose are detected to be loaded into the sample transport system in question. Incidentally, the group management control information is made up of group fields including group information 1 (group start sample), group information 2 (group target sample), and group information 3 (group end sample).

FIG. 2 shows an example of group management information to be set at the sample loading section when samples 1 through 4 and samples 6 and 7 collected from the same patient are targeted for the same test purpose.

Upon detection of the loading of multiple test tube samples by the sample loading section, group information is added to the samples making up the multiple test tube samples. This embodiment has group information 1 set for sample 1, group information 2 set for samples 2 and 3, and group information 3 set for sample 4 thereby to provide group management of samples 1 through 4. Likewise, group information 1 is set for sample 6 and group information 3 is set for sample 7 so that samples 6 and 7 may be placed under group management. No group information is set for sample 5 that need not be placed under group management. These items of group information may be stored directly into radiofrequency identifiers (RFIDs) retained by sample holders that hold and transport samples, or stored into a host computer along with sample identifier (ID) information for reference as needed.

Meanwhile, in FIG. 2, a pre-treatment unit A, as indicated in a unit designation row 203, to which the sample loaded by the samples loading section are transported, references the group information in the group management control information upon receipt of sample 1. Since group information 1 is set for sample 1, sample 1 is made to wait at the converging point 13 established on this pre-treatment unit. Also, any other carrier not belonging to the same group as that of sample 1 is inhibited from cutting in.

When samples 2 and 3 are transported to the converging point 13 at which sample 1 is placed in a wait state, and when their group information turns out to be group information 2 upon reference thereto, samples 2 and 3 are also made to wait at the converging point 13 along with sample 1. Later, upon receipt of sample 4, a reference is made to the group information in the group management control information so as to verify that group information 3 is being set. Once group information 1 through 3 has all been ascertained, the wait state of samples 1 through 3 at the converging point 13 established on the above-mentioned pre-treatment unit is cancelled, and the samples are transported to the processing section 15 of the unit. The cancellation of the wait state should preferably be subject to time-out surveillance so as to avoid the conveyor line being locked up.

Meanwhile, as indicated at unit designation row 203 of FIG. 2, a pre-treatment unit B provides group management of samples 1, 2 and 4 but does not place sample 3 under group management because the group information on sample 3 does not stipulate group management by the pretreatment unit B. In this case, the group management information is again set for samples 1 through 4 at a branching point 14 of the pre-treatment unit which precedes the pre-treatment unit B (e.g., pre-treatment unit A) and to which the samples are to be transported beforehand. Specifically, group information 1 is set for sample 1, group information 2 is set for sample 2, and group information 3 is set for sample 4; no group information is set for sample 3 alone. This makes it possible flexibly to create and manage the sample group in accordance with the sample type and the detailed processing by pre-processing units.

Figure 3:
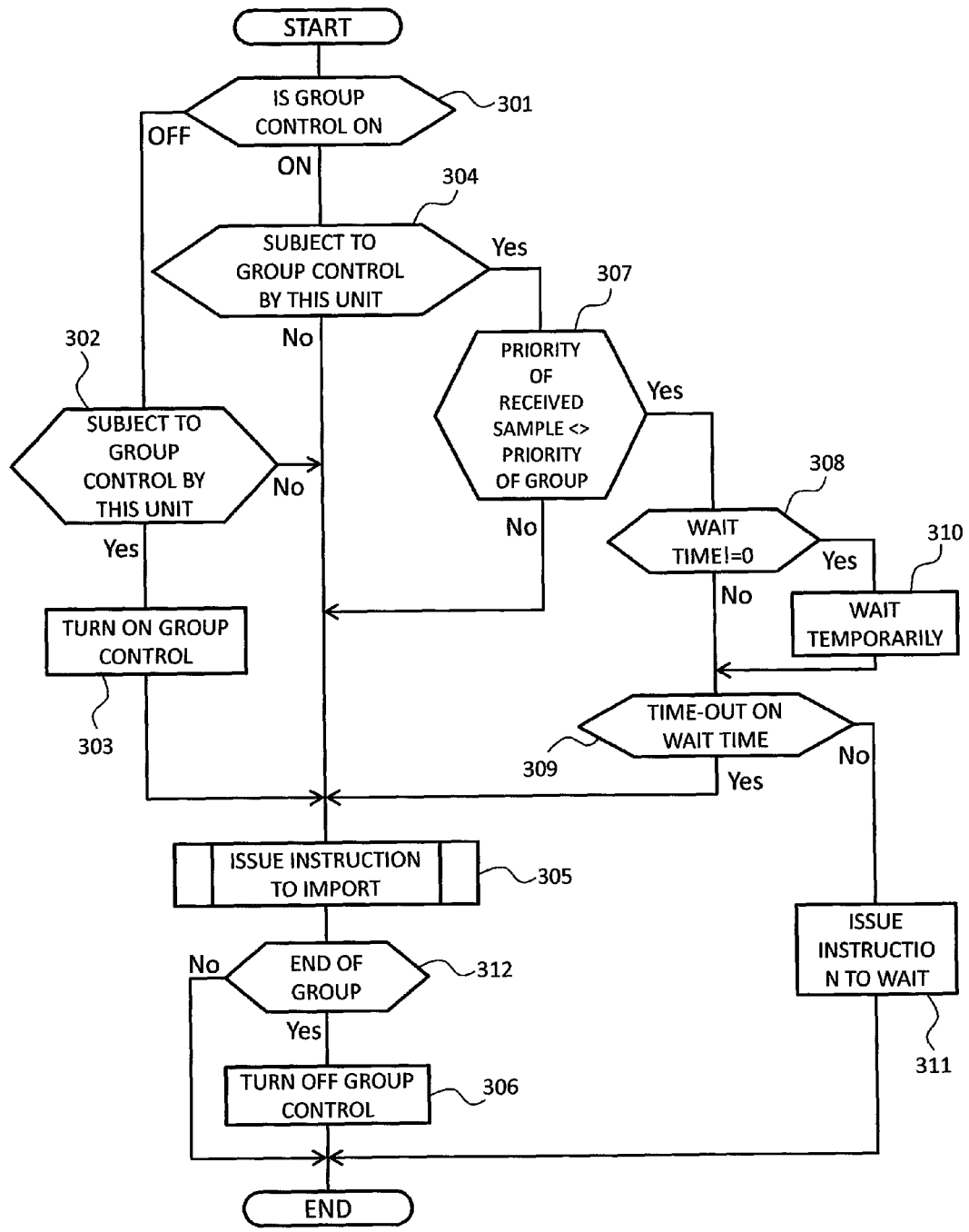
FIG. 3 shows a flow of import processing at a converging point.

FIG. 3 explains a flow at a converging point of the processing of samples being imported into a pre-treatment unit. When a sample is transported to a pre-treatment unit, it is determined whether group control is turned ON (step 301).

If group control is ON, it is determined whether the imported sample is subject to group control by the pre-treatment unit in question (step 304). Whether or not the sample is subject to group control is determined by whether the group management control information has this pre-treatment unit designated in unit designation information 203 for group management control of the imported sample.

If the sample is subject to group control by the pre-treatment unit in question, the group priority under group control (the import priority in the group management control information) is compared with the priority of the received sample (step 307), so as to determine whether the priority differs from that of the group samples being processed. If the priority of the received sample is equal to the import priority, the sample is imported (step 305). If the priority of the received sample is different from the import priority, the wait time is verified (step 308), and the arrival of a sample subject to group management is awaited from another line for a predetermined time period (step 310). Following determination of the arrival of such a group-managed sample and a time-out on the wait time (step 309), step 305 is reached and the sample in question is imported. As needed, the sample of interest may be allowed to wait without being imported even in the event of a time-out on the wait time (step 311).

If group control is not turned ON, it is determined whether the sample should be subjected to group control by this unit (step 302). If the sample is to be subjected to group control by this unit, group control is turned ON in step 303 and the sample is imported in step 305. On the other hand, if the sample is not to be subjected to group control by this unit, group control is not turned ON and an instruction to import this sample is issued (step 305). Upon completion of the import of the sample in question, the samples making up the group are considered to have come to an end (step 312), and group control is turned OFF (step 306).

When group management control is performed in this manner, the samples targeted for the same processing purpose can be imported consecutively into the unit.

As a result of this, the multiple test tube samples transported to any one of the pre-treatment units are made to wait temporarily at the converging point 13. When all of the multiple test tube samples have arrived, they are transported to the unit processing section 15. Because a plurality of samples destined for the same process are transported as a group, when all test tubes that need to be decapped are loaded as a group into the unit processing section 15 of an decapping unit capable of decapping multiple test tubes simultaneously, it is possible to make maximum use of the processing capability of the decapping unit.

Also, if the present invention is applied to an aliquoting unit and if multiple test tube samples for which group management information has been set are transported to that aliquoting unit, it is possible not only to make maximum use of the processing capability of the aliquoting unit but also to eliminate the process of manual aliquoting of any sample to be aliquoted additionally for lack of amount. In the case of a system incapable of group management control, an aliquoting error occurs if the amount of sample to be aliquoted from a first test tube is insufficient, which requires the operator to perform manual aliquoting. However, with group management control in effect, if samples collected from one patient for the same test purpose are placed in, say, three test tubes, these test tubes may be transported as a group to the aliquoting unit. In this case, if the amount of sample to be aliquoted from the first test tube is insufficient, the lacking amount can be sucked from the second or the third test tube and aliquoted into an aliquot sample container.

Also, there is no need to use a newly prepared aliquot test tube on which a chip or a sample label is to be pasted for aliquoting use. This leads to savings in consumables.

However, with the above-mentioned sample transport system, if the sequence of samples under group management control is disrupted due to a system error or the like, or if samples subject to group management have failed to be loaded consecutively, it is impossible to perform group management control. In order to avoid such contingencies, a wait buffer 16 should preferably be set up additionally near the converging point 13, the buffer being arranged to accommodate samples to be imported or exported and to allow the samples to wait therein. Upon detection of a series of samples subject to group management control, the wait buffer 16 allows the samples to wait therein temporarily. Once all samples subject to group management control have arrived, group management control information is again created for the group of these samples in the same manner as at the branching point 14. This makes it possible consecutively to transport the samples subject to group management to the processing section 15 of the pre-treatment unit, whereby processing efficiency is improved.

It is rare for the objects under group management control to be handled entirely by the system; differences exist depending on the system configuration and processing operation. Generally, where group management control is performed on samples moving from the loading section up to a storing section, ordinary samples not subject to group management are restricted from using the converging point 13. Thus in the case of an urgent sample not subject to group management control, the reporting of the result of sample tests could be delayed.

For example, although processing efficiency can be improved when the aliquoting unit performs multiple test tube sample processing, the multiple test tube sample processing under group management is not needed for the units not requiring high-speed processing, such as the decapping unit or storage unit that handles test tubes one at a time. In another example, when samples are loaded, they may be transported to a centrifugal unit processing section that processes dozens of test tubes simultaneously. When the samples are exported from the centrifugal unit following the centrifugal process, the management section 100 may reference the request information on the multiple test tube samples targeted for the same process, create group management information only for those destined for the aliquoting unit, and reset the group management information on the samples at the branching point of the aliquoting unit. In this manner, the multiple test tube samples are not placed needlessly under group management by the pre-treatment units that do not perform high-speed processing (e.g., decapping unit and storage unit), which in turn allows ordinary samples to be restricted less frequently from using the converging point 13. This helps prevent delayed reporting of the test results of ordinary samples not subject to group control.

Thus with regard to the samples that need group management control, the management section 100 designates the range in which group management control is necessary for the samples involved at the branching point 14 of each pre-treatment unit. Specifically, when setting group fields, the management section 100 adds information designating the units that will place the multiple test tube samples of interest under group management. This makes it possible to reduce the occupancy rate, at the converging point, of the samples subject to group management control as opposed to other ordinary samples. In FIG. 2, the unit designation information 203 represents the added designating information.

Furthermore, if an ordinary sample not subject to group management control is an urgent sample, that sample should be given priority over the samples subject to group management control. In such a case, the above-mentioned wait buffer 16 established near the converging point 13 may be used temporarily to save the group-managed samples therein. This makes it possible for the sample transport system to receive temporarily the urgent sample not subject to group management, thereby shortening the turn-around time (TAT) of the priority sample.

Likewise, if the samples subject to group management control are urgent samples, they are further given import priority information 204 and export priority information 205 constituting the group management control information as shown in FIG. 2. This makes it possible to transport and process these samples subject to group management control in preference to the other samples under group management control to which ordinary priority has been established.

Incidentally, the above-mentioned sample transport system may internally contain a plurality of groups of samples subject to group management. If that is the case, the priorities given to each sample group may be compared with one another so as to prioritize the groups for transportation and processing. For example, suppose that there are established import priorities 1 through 10 (the nearer the 10, the higher the priority for import) and export priorities 1 and 2 (priority 2 is higher than priority 1 for export). In FIG. 2, import priority 1 and export priority 1 are set for samples 1 through 4, and import priority 10 and export priority 2 are set for samples 6 and 7.

However, only with the above-described control method, the sequence of samples subject to group management control can be broken halfway. Following the breakup, the remaining samples subject to group management control are to be handled as ordinary samples.

In order to avoid such a situation, the wait buffer 16 should preferably be set up near the converging point 13 of the above-mentioned sample transport system. The pre-treatment unit equipped with this wait buffer causes as many samples as can be processed simultaneously by the pre-treatment unit to wait in the buffer. When the designated number of samples has arrived, they are exported in accordance with the flow of converging point export processing. Explained below in reference to FIG. 4(*a*) is such a flow of converging point export processing.

In step 401, the presence or absence of a sample to be imported into the pre-treatment unit of interest is detected. For example, a sensor may be used to detect whether a sample which was processed by another pre-treatment unit located upstream of this pre-treatment unit and which is to be transported to this pre-treatment unit, has been exported from the preceding pre-treatment unit.

A comparison is made between the import priority information 204 on the sample detected in step 401 to be imported into this pre-treatment unit on the one hand, and the export priority information 205 on the sample placed in a wait state in the wait buffer of this pre-treatment unit on the other hand (step 402). If the import priority information 204 is of a higher priority than the export priority information 205, the sample is imported into this pre-treatment unit (step 411).

Figures 4A, 4B:
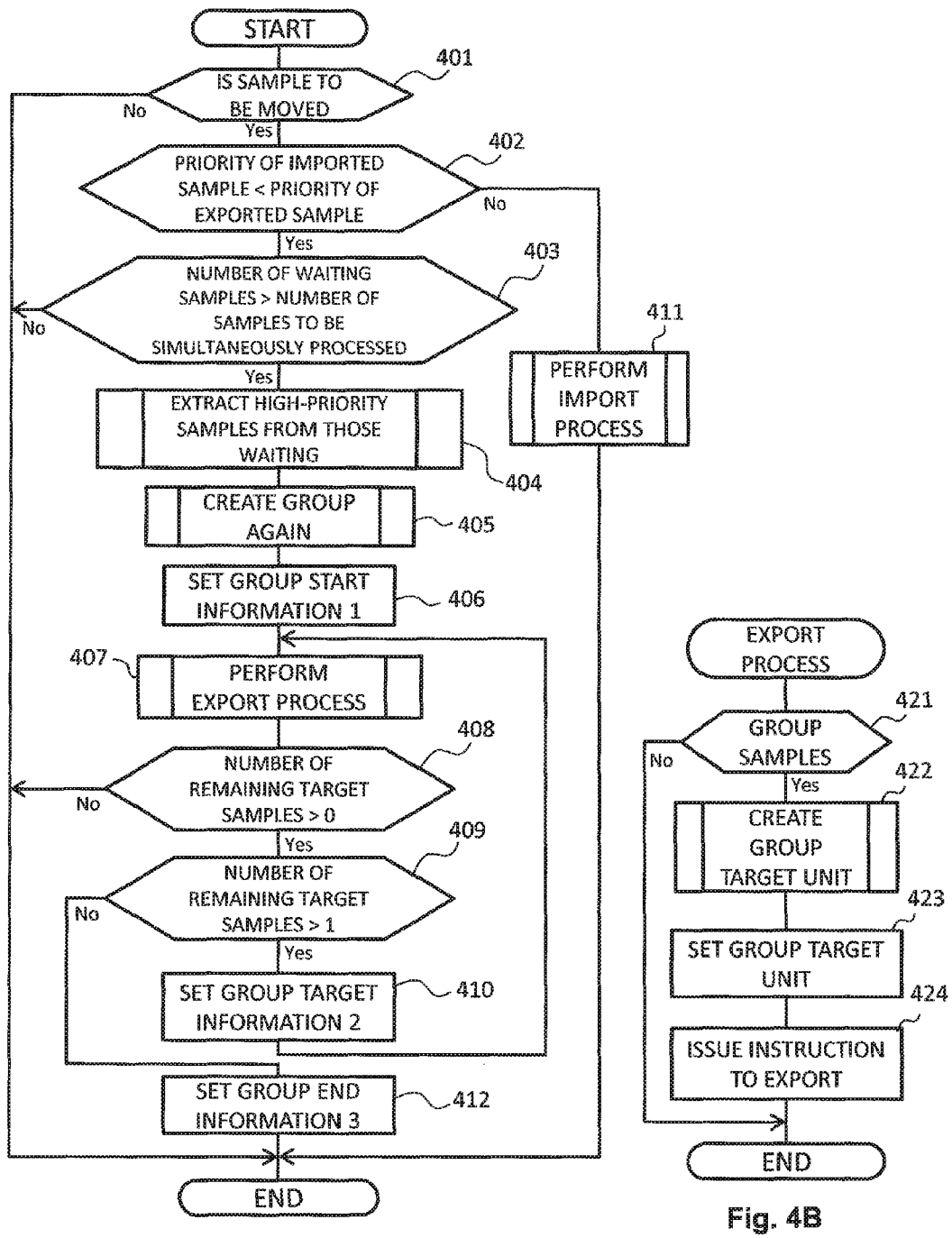
FIGS. 4A and 4B show flows of export processing at the converging point.

On the other hand, if the export priority information 205 is of a higher priority than the import priority information 204, the import process is not carried out. In this case, the number of samples waiting in the wait buffer is compared with the number of samples that can be processed simultaneously by this pre-treatment unit (step 403). If the number of samples that can be processed simultaneously is smaller than the number of waiting samples, step 404 is reached. In step 404, the management section 100 determines the number of carriers to be exported from the converging point 13 based on the number of samples that can be processed simultaneously by this pre-treatment unit. In step 405, the group management control information such as is shown in FIG. 2 is again created. In designating the group management information, the first of the samples to be managed as a group is set with group management information 1 (step 406). Thereafter, the export process is performed (step 407). A detailed export process is carried out as shown in FIG. 4(*b*), to be discussed later. If there remain at least two samples after the first sample has been exported (steps 408, 409), group target information 2 is set for these samples (step 410). If there remains one sample (step 409), group target information 3 is set for this sample (step 412). The export process (step 407) is carried out in this manner. In the export process shown in FIG. 4(*b*), every time a sample is exported from the converging point 13 to the unit processing section 15, the unit that should process the sample is identified (step 422), the target unit designation information 203 in FIG. 2 is set for the group management control information (step 423), and the carrier is exported (step 424). Meanwhile, those samples not requiring group management processing by the pre-treatment unit to which they are to be transported next are given a "No" determination in step 421, and the group information and the unit information subject to group management are not set. This makes it possible for each unit consecutively to export from the converging point 13 as many samples subject to group management control as the number of samples that can be processed simultaneously by the unit.

Furthermore, if the waiting capacity of the above-mentioned wait buffer 16 is enlarged, it is possible for the buffer to hold a plurality of groups of samples or ordinary samples in a temporary wait state. Further, if the export priority information 205 is further divided, it is possible to export the sample groups in prioritized order.

Figure 6:
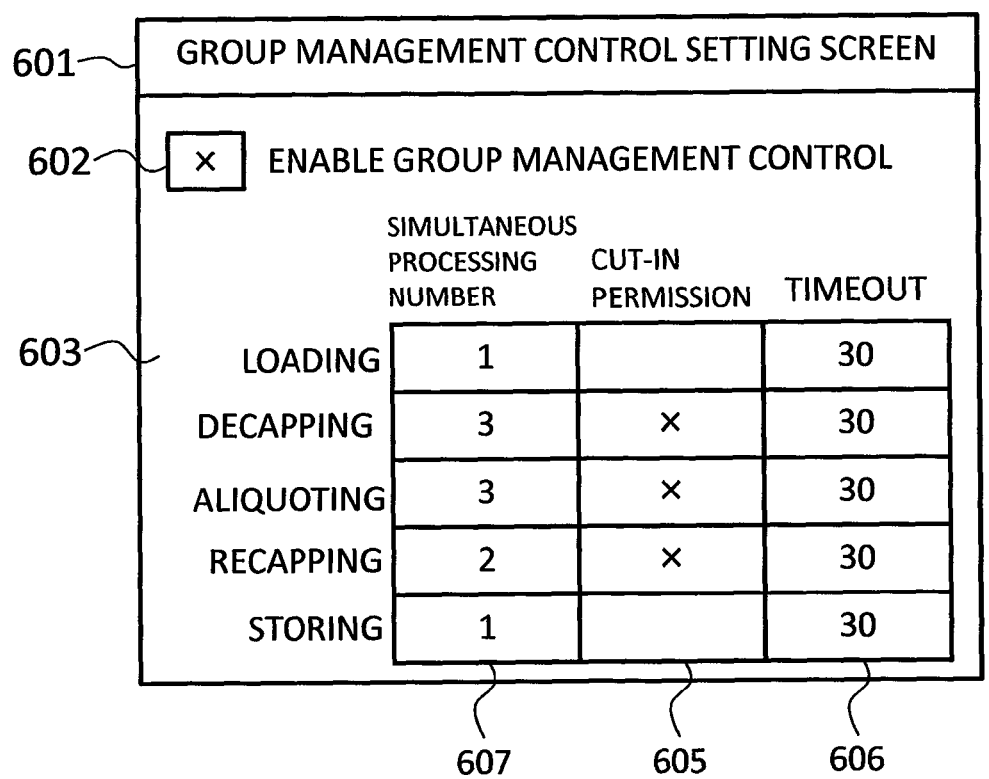
FIG. 6 shows a group management control setting screen.

FIG. 6 shows a group management information setting screen, and the group management information that can be set by the operator is explained below.

On a group management setting screen 601, a selectable control 602 enables user activation or deactivation of group management control, and an area 603 displays the names of the units such as the sample loading section, decapping unit, aliquoting unit, recapping unit, and sample storing section that make up the sample transport system. Additionally, a sample labeler and a centrifugal separation unit may be displayed in this area.

For each of the pre-treatment units, it is possible to set a simultaneous processing count 607, cut-in permission 605, and a time-out time 606.

The simultaneous processing count 607 indicates the number of samples that can be processed simultaneously by each pre-treatment unit. For example, for an decapping unit capable of decapping three samples simultaneously, the simultaneous processing count is set to 3.

The cut-in permission 605 is set to determine whether or not to permit the cut-in of another sample that is not subject to group management and that has been transported to the samples subject to group management while the samples are placed in a wait state at the converging point or the like. For example, in the case of FIG. 6, the cut-in of another sample is not permitted for the decapping unit, aliquoting unit, and recapping unit.

The time-out time 606 indicates a maximum time period allowed to elapse from the time the first of the samples subject to group management is transported to the wait buffer 16 attached to each pre-treatment unit, until the time all of the samples subject to group management have arrived. In FIG. 6, the time-out time is set to 30 minutes for all pre-treatment units. Thus if not all of the samples subject to group management have arrived in 30 minutes, these samples are no longer subject to group management and will be processed individually.

Although the embodiment above was shown to be a sample transport system to which the present invention is applied and which performs pre-treatment before analyzing samples, the embodiment is not limitative of this invention. For example, the invention is also effective when applied to an analyzing system to which a plurality of analyzing units for analyzing samples are connected. Specifically, consider applying this invention to group management of calibrators or accuracy control samples loaded into a system. Normally, upon execution of calibration, a plurality of types of calibrators are analyzed, and the concentration levels of the calibrators are matched against the results of the analysis to create the calibration curve. If this invention is applied to the execution of calibration, a plurality of calibrators may be subjected to group management and measured as a group. When the calibrators are measured as a group, it is possible to prevent calibration errors such as the unavailability of calibration due to a part of calibrators being withheld mistakenly from getting loaded.

DESCRIPTION OF REFERENCE NUMERALS 1, 2, 3 Pre-treatment unit
11, 507 Conveyor line
12, 506 Connecting line
13, 508 Converging point
14, 509 Branching point
15 Unit processing section
16 Wait buffer
100 Management section
201 Sample ID in group management control information
202 Group designation information in group management control information
203 Unit designation information in group management control information
204 Priority Information in group management control information
501 to 505 Processing Unit
510 Return line
601 Group management control setting screen

The invention claimed is:

1. A sample transport system comprising:
a plurality of processing units to perform processing on testing samples, and
a plurality of conveyor lines configured to transport carriers, each carrier carrying a respective testing sample;
a converging point configured to receive the carriers from at least two of the conveyor lines and transmit the carriers to one of the processing units via a single one of the conveyor lines;
a buffer connected with the converging point and configured to store one or more of the carriers carrying respective testing samples; and
a manager connected with a memory that is configured to maintain group managing information in accordance with whether a plurality of testing samples on a plurality of carriers are to be transported in succession;
wherein the manager is programmed to determine, based on the group managing information, whether:
(a) a first one of the carriers at the converging point is to be stored in the buffer to wait for other carriers that are treated as a same group with the first carrier, and then transported in succession with the other carriers so as to be treated as the same group, or
(b) the first carrier at the converging point is to be transported to the one of the processing units individually.

2. The sample transport system according to claim 1, wherein:
the plurality of conveyor lines include a main conveyor line that conveys the carriers in a direction from an upstream location toward a downstream location, and connecting lines which convey one or more of the carriers toward or away from the main conveyor line,
the processing units are arranged along the main conveyor line and furnished with a processing mechanism which performs processing on one or more of the samples, and
the converging point is located on an upstream side of the processing mechanism at a first connection part of the main conveyor line and a first connecting line that conveys the one or more carriers toward the main conveyor line.

3. The sample transport system according to claim 2, further comprising:
a branching point located on a downstream side of the processing mechanism at a second connection part of the main conveyor line and a second connecting line that conveys the one or more carriers away from the main conveyor line,
wherein the manager is programmed to determine whether the sample on an individual carrier at the branching point is to be processed consecutively with the sample on at least one other carrier by a next processing unit to which the individual carrier is to be transported next, and if so, to set group management information for managing the sample on the individual carrier at the branching point as included in the same group with the sample on the at least one other carrier.

4. A control method for a sample transport system including a plurality of conveyor lines which transport carriers carrying test tubes holding testing samples, and a plurality of units each furnished with a processing section which performs processing on one or more of the testing samples carried by the carriers, the control method comprising:
creating sample group information for consecutively transporting a plurality of samples based on information that the plurality of samples are related to each other;
providing the sample group information to the plurality of units; and
transporting the plurality of samples on at least one of the conveyor lines so that the units consecutively receive a plurality of the carriers, carrying the plurality of samples, based on the sample group information, wherein the plurality of units include a simultaneous processing unit capable of simultaneously processing multiple samples, wherein the transporting the plurality of samples on at least one of the conveyor lines comprises transporting the plurality of samples on a main conveyor line in a direction from upstream to downstream, wherein the main conveyor line includes a converging section where a connecting conveyor line connects to the main conveyor line, and wherein the converging section is upstream of the simultaneous processing unit, the control method further comprising:

providing the sample group information to the simultaneous processing unit for processing the plurality of samples consecutively;

receiving one or more of the plurality of carriers at the converging section via the connecting conveyor line; and transporting consecutively the one or more received carriers with the plurality of carriers to the processing section of the simultaneous processing unit to be processed simultaneously.

5. The control method for a sample transport system according to claim 4, wherein there is provided, at the converging section, a carrier wait mechanism, the control method further comprising:

causing transport of a least one carrier of the plurality of carriers to be delayed temporarily in the carrier wait mechanism; and transporting the at least one delayed carrier consecutively with others of the plurality of carriers to the processing section of the simultaneous processing unit based on the sample group information.

6. The control method for a sample transport system according to claim 5, further comprising providing a wait buffer which is located near the converging section as the wait mechanism, wherein the wait buffer is configured to temporarily hold one or more carriers therein.

7. The control method for a sample transport system according to claim 4, further comprising:

creating the sample group information for a start unit and an end unit of the plurality of units, wherein the sample group information enables controlling a group of samples comprising the plurality of samples;

removing at least one sample from the group of samples following processing at the end unit; and preventing a carrier excluded from the sample group information from interrupting consecutive ordering of the plurality of carriers during transport of the plurality of carriers to a next unit after the end unit.

8. The control method for a sample transport system according to claim 7, further comprising:

creating the sample group information supplemented with priorities;

comparing, at the converging section, the plurality of carriers with another carrier based on the priorities to determine whether to permit the other carrier to be transported ahead of the plurality of carriers; and based on the other carrier carrying a sample with higher priority than the samples carried by the plurality of carriers, causing the other carrier to be transported ahead of the plurality of carriers to the processing section of the simultaneous processing unit downstream of the converging section.

9. The control method for a sample transport system according to claim 4, further comprising:

creating the sample group information supplemented with priorities;

comparing, at the converging section, the plurality of carriers to be processed simultaneously with another carrier based on the priorities to determine whether to permit the other carrier to be transported ahead of the plurality of carriers; and based on the other carrier carrying a sample with a higher priority than the samples carried by the plurality of carriers, causing the other carrier to be transported ahead of the plurality of carriers to the processing section of the simultaneous processing unit downstream of the converging section.

10. The control method for a sample transport system according to claim 9, further comprising:

causing, at the converging section, at least some of the plurality of carriers to be delayed in the carrier wait mechanism, wherein the plurality of carriers designated for simultaneous processing are divided by the wait mechanism into a first portion and a second portion.

* * * * *